United States Patent [19]
Bueschken et al.

[11] Patent Number: 5,756,856
[45] Date of Patent: May 26, 1998

[54] PROCESS FOR THE PREPARATION OF 2-ETHYLHEXANAL

[75] Inventors: Wilfried Bueschken, Haltern; Juergen Hummel, Marl, both of Germany

[73] Assignee: Huels Aktiengesellschaft, Marl, Germany

[21] Appl. No.: 668,355

[22] Filed: Jun. 26, 1996

[30] Foreign Application Priority Data

Jul. 8, 1995 [DE] Germany ............ 195 24 970.4

[51] Int. Cl.$^6$ ............................................. C07C 45/62
[52] U.S. Cl. ............................................. 568/462
[58] Field of Search ............................ 568/462, 396

[56] References Cited

U.S. PATENT DOCUMENTS

| | | | |
|---|---|---|---|
| 2,825,743 | 3/1958 | Mac Lean et al. | 568/462 |
| 3,361,822 | 1/1968 | Schmitt et al. | 568/396 |
| 3,903,171 | 9/1975 | Toussaint et al. | 568/462 |
| 4,018,831 | 4/1977 | Bowes, et al. | 568/462 |
| 4,273,945 | 6/1981 | Heilen et al. | 568/462 |
| 4,394,525 | 7/1983 | Vogel et al. | 568/462 |
| 4,450,300 | 5/1984 | Fischer et al. | 568/462 |

FOREIGN PATENT DOCUMENTS

| | | |
|---|---|---|
| 0 011 906 | 6/1980 | European Pat. Off. |
| 0 541 871 | 5/1993 | European Pat. Off. |
| 1 941 634 | 11/1970 | Germany |
| 2 008 128 | 9/1971 | Germany |
| 781 405 | 8/1957 | United Kingdom |
| 1 032 838 | 6/1966 | United Kingdom |
| 87 07598 | 12/1987 | WIPO |

*Primary Examiner*—James H. Reamer
*Attorney, Agent, or Firm*—Oblon, Spivak, McClelland, Maier & Neustadt, P.C.

[57] ABSTRACT

The present invention relates to a process for the preparation of 2-ethylhexanal by catalytic hydrogenation of 2-ethylhex-2-enal, wherein the hydrogenation is carried out in a plurality of two or more series-connected loops, wherein each loop involves the use of one reactor, which comprises:

(a) feeding 2-ethylhex-2-enal and hydrogen to an upper part of a reactor to catalytically hydrogenate said 2-ethylhex-2-enal to produce a hydrogenation product, (b) recycling a portion of said hydrogenation product back into said upper part of said reactor, (c) feeding the remainder of said hydrogenation product from said reactor to an upper part of a subsequent reactor wherein 2-ethylhex-2-enal is catalytically hydrogenated to produce a subsequent hydrogenation product, and wherein a portion of said subsequent hydrogenation product has been recycled and is fed with said remainder of said hydrogenation product to said upper part of said subsequent reactor, (d) repeating step (c) until the subsequent reactor is the last reactor, (e) recovering the remainder of said subsequent hydrogenation product from said last reactor, and (f) obtaining 2-ethylhexanal from the product of step (e).

20 Claims, 1 Drawing Sheet

PROCESS FOR THE PREPARATION OF 2-ETHYLHEXANAL

BACKGROUND OF THE INVENTION

1. Field of the Invention

The present invention relates to a process for the preparation of 2-ethylhexanal by catalytic hydrogenation of 2-ethylhex-2-enal.

2. Description of the Background

2-Ethylhexanal is used for the synthesis of perfumes and is a precursor of 2-ethylhexanoic acid.

Processes for the continuous preparation of 2-ethylhexanal by catalytic hydrogenation of 2-ethylhexenal are known.

In order to achieve virtually complete conversion in a continuous hydrogenation, there are in principle two processes:

a) Hydrogenation is performed in a tubular reactor (reaction tube of sufficient length) in straight flow-through.

b) Hydrogenation is performed in two reactors. The first reactor, which is generally operated in a loop procedure, is followed by a second reactor, in which hydrogenation is performed in straight flow-through, for finishing.

DE-A 19 41 634 claims the hydrogenation on a specially prepared Pd/SiO$_2$ catalyst. The reaction is carried out in a single-stage loop procedure. The throughputs are between 0.4 and 0.6 kg/l of catalyst ·h. According to the example, at a conversion rate of 99.1%, the selectivity for 2-ethylhexanal is 97.8%.

DE-A 20 08 128 describes a single-stage loop process in which the use of an area velocity of the catalyst of 10 –50 m/h is emphasized as a particular advantage. At a throughput of 0.325 l/kg of catalyst ·h, a conversion rate of 99.2% is achieved. No information as to selectivity is available.

In the two above-mentioned publications, the space-time yield is too low from an economic aspect.

U.S. Pat. No. 4,018,831 describes the liquid-phase hydrogenation on a nickel catalyst. At a throughput of 1.1 kg/kg of catalyst ·h, a virtually 100% conversion rate and a selectivity of 97.5% are achieved. Here, the selectivity is unsatisfactory.

The object of the present invention was therefore to provide a process which enables 2-ethylhexanal to be prepared in an economical manner and with high selectivity by catalytic hydrogenation of 2-ethylhex-2-enal.

SUMMARY OF THE INVENTION

It has now surprisingly been found that virtually complete conversion and outstanding selectivity are achieved if the catalytic hydrogenation is carried out in a plurality of series-connected loops, preferably in a double loop procedure. In a suitable procedure, 2-ethylhex-2-enal is fed into a portion of the hydrogenation discharge from the first reactor and this mixture is passed to the top of the first reactor. Hydrogenation product is passed under level control from the hydrogenation reservoir of the first reactor into the loop of the second reactor. This mixture flows to the top of the second reactor. Hydrogenation material is removed under level control from the hydrogenation reservoir of the second reactor.

DESCRIPTION OF THE PREFERRED EMBODIMENTS

Figure 1:
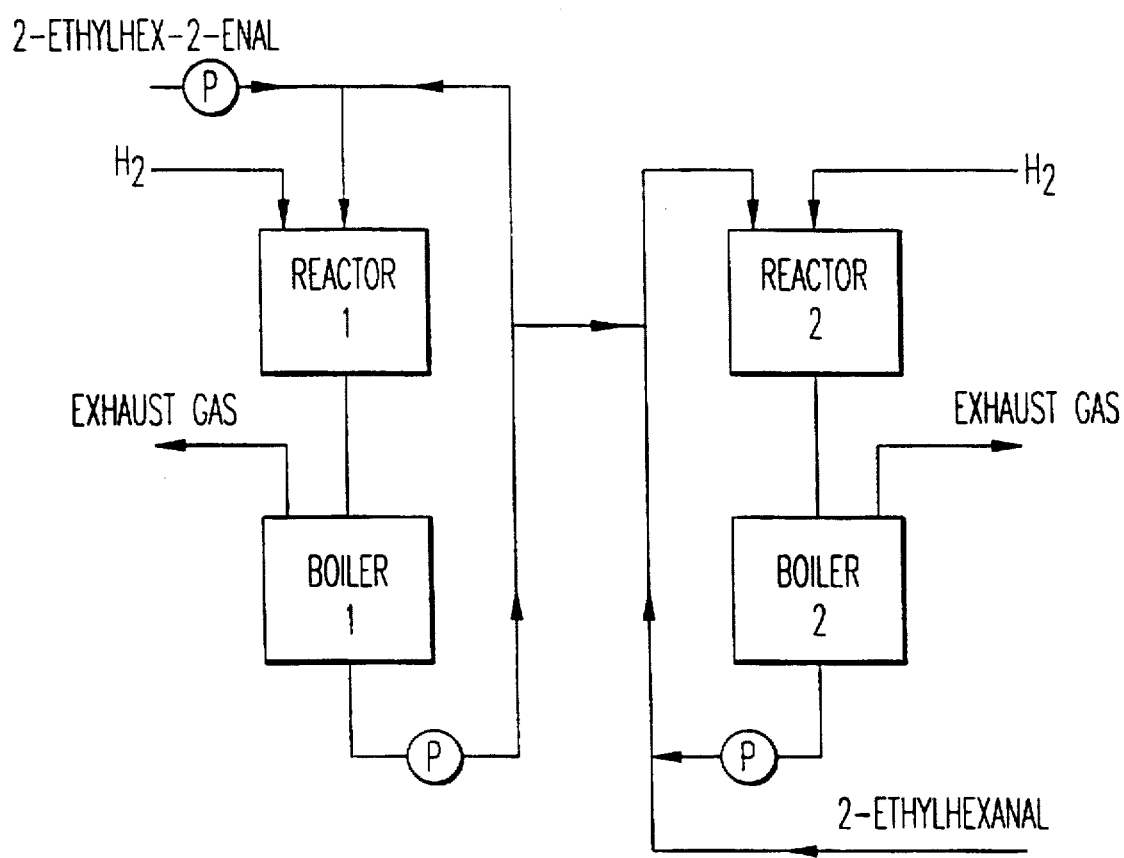
FIG. 1 is a block diagram illustrating the process of the invention.

The present process, for example using a double loop procedure, has the advantage over the conventional procedure (1st stage loop; 2nd stage straight flow-through) that, for the same amount of catalyst (sum of the amounts in both reactors), the production rate can be increased by more than 30%. At conversion rates of above 99.9%, the selectivities achieved for 2-ethylhexanal are over 99%.

The present invention therefore relates to a process for the preparation of 2-ethylhexanal by catalytic hydrogenation of 2-ethylhex-2-enal, wherein the hydrogenation is carried out in a plurality of two or more series-connected loops, wherein each loop involves the use of one reactor, which comprises:

(a) feeding 2-ethylhex-2-enal and hydrogen to an upper part of a reactor to catalytically hydrogenate said 2-ethylhex-2-enal to produce a hydrogenation product, (b) recycling a portion of said hydrogenation product back into said upper part of said reactor, (c) feeding the remainder of said hydrogenation product from said reactor to an upper part of a subsequent reactor wherein 2-ethylhex-2-enal is catalytically hydrogenated to produce a subsequent hydrogenation product, and wherein a portion of said subsequent hydrogenation product has been recycled and is fed with said remainder of said hydrogenation product to said upper part of said subsequent reactor, (d) repeating step (c) until the subsequent reactor is the last reactor, (e) recovering the remainder of said subsequent hydrogenation product from said last reactor, and (f) obtaining 2-ethylhexanal from the product of step (e).

In the process of the invention, the hydrogenation is preferably carried out in two series-connected loops; 2-ethylhex-2-enal, together with a portion of the hydrogenation product from the first reactor, being passed to the top of the first reactor, the remainder of the hydrogenation product from the first reactor, together with a portion of the hydrogenation product from the second reactor, being passed to the top of the second reactor, and 2-ethylhexanal being obtained from the remainder of the hydrogenation product from the second reactor.

In the process of the invention, the hydrogenation can be carried out either in turbulent or in laminar flow in all reactors. It is also advantageous to carry out the hydrogenation in turbulent flow at least in the first reactor. Furthermore, the hydrogenation is preferably carried out in the liquid phase in all reactors.

In the process of the invention, the hydrogenation is preferably carried out at temperatures of 40° to 150° C., particularly preferably at temperatures of 80° to 130° C. In addition, it can be advantageous to carry out the hydrogenation in the reactors at different temperature levels, for example by operating the second or subsequent reactor at a lower temperature than the first or preceding reactor.

Generally, the process of the invention is performed under pressure. Preferably, the hydrogenation is carried out here in the reactors at pressures of 1 to 100 bar absolute, particularly preferably at pressures of 5 to 20 bar absolute. Furthermore, it can be advantageous to carry out the hydrogenation in the reactors of the process of the invention at different pressure levels, for example by operating the second or subsequent reactor at a lower pressure than the first or preceding reactor.

As the catalyst charge in the reactors, customary hydrogenation catalysts suitable for this can be used.

In the process of the invention, the hydrogenation is preferably carried out in the reactors on a palladium catalyst, particularly preferably on a palladium catalyst applied to a support of aluminum oxide, for example 0.5% Pd/Al$_2$O$_3$, (Engelhard).

The process of the invention enables particularly economical preparation of 2-ethylhexanal with very good yield and outstandingly high selectivity.

Having generally described this invention, a further understanding can be obtained by reference to certain specific examples which are provided herein for purposes of illustration only and are not intended to be limiting unless otherwise specified.

EXAMPLES

Example 1

The hydrogenation apparatus, as shown in FIG. 1, has two reactors of the same type with the following dimensions:

$\phi_c$=42 mm; 1=1500 mm. The two reactors are each packed with 1.9 l of catalyst (0.5% Pd/Al$_2$O$_3$).

Technical-grade 2-ethylhexenal (96% 2-ethylhexenal, 0.02% 2-ethylhexanol), diluted with partially hydrogenated starting material (from boiler 1), is passed to the top of the first reactor (1st loop).

From boiler 1, hydrogenation material is passed under level control into the loops of the second reactor. Technical-grade 2-ethylhexanal is removed under level control from boiler 2.

The following reaction conditions are present in the reactors:

|  | Reactor 1 | Reactor 2 |
| --- | --- | --- |
| Throughput | 6.19 kg/h | 6.26 kg/h |
| Circulation | 130 kg/h | 65 kg/h |
| H$_2$ pressure | 15 bar | 15 bar |
| Mean temperature | 124° C. | 116° C. |
| Exhaust gas rate | 220 l(S.T.P.)/h | 110 l(S.T.P.)/h |

After a quasi steady-state has been established, a hydrogenation material of the following quality is obtained:

| 2-ethylhexenal | 0.09% by weight |
| --- | --- |
| 2-ethylhexanal | 95.46 by weight |
| 2-ethylhexanol | 0.46 by weight |

This corresponds to a conversion rate of 99.9% and a selectivity of 99.4%.

Comparison example

In contrast to Example 1, the circulation of the second reactor is switched off (circulation rate 0). Keeping to the boundary conditions (conversion rate>99.9% and selectivity>99%) and aiming at the highest possible throughput, the following reaction conditions were found:

|  | Reactor 1 | Reactor 2 |
| --- | --- | --- |
| Throughput | 4.74 kg/h | ≦4.79 kg/h |
| Circulation | 130 kg/h | 0 kg/h |
| H$_2$ pressure | 15 bar | 15 bar |
| Mean temperature | 100° C. | 90° C. |
| Exhaust gas rate | 160 l(S.T.P.)/h | 60 l(S.T.P.)/h |

It follows from this that when the double loop procedure is used, 30% more 2-ethylhexanal can be produced in the present apparatus.

The disclosure of German patent application 195 24 970.4, filed Jul. 8, 1995, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the preparation of 2-ethylhexanal by catalytic hydrogenation of 2-ethylhex-2-enal, wherein the hydrogenation is carried out in a plurality of two or more series-connected loops, wherein each loop involves the use of one reactor, which comprises:

(a) feeding 2-ethylhex-2-enal and hydrogen to an upper part of a reactor containing a hydrogenation catalyst to catalytically hydrogenate said 2-ethylhex-2-enal at 40° to 150° C. and 1 to 100 bar absolute to produce a hydrogenation product, (b) recycling a portion of said hydrogenation product back into said upper part of said reactor, (c) feeding the remainder of said hydrogenation product from said reactor to an upper part of a subsequent reactor containing a hydrogenation catalyst wherein 2-ethylhex-2-enal is catalytically hydrogenated at 40° to 150° C. and 1 to 100 bar absolute to produce a subsequent hydrogenation product, and wherein a portion of said subsequent hydrogenation product has been recycled and is fed with said remainder of said hydrogenation product to said upper part of said subsequent reactor, (d) repeating step (c) until the subsequent reactor is the last reactor, (e) recovering the remainder of said subsequent hydrogenation product from said last reactor, and (f) obtaining 2-ethylhexanal from the product of step (e).

2. The process as claimed in claim 1, wherein the hydrogenation is carried out in two series-connected loops.

3. The process as claimed in claim 1, wherein hydrogenation is performed in the liquid phase in all reactors.

4. The process as claimed in claim 2, wherein hydrogenation is performed in the liquid phase in all reactors.

5. The process as claimed in claim 1, wherein the flow is laminar in all reactors.

6. The process as claimed in claim 2, wherein the flow is laminar in all reactors.

7. The process as claimed in claim 3, wherein the flow is laminar in all reactors.

8. The process as claimed in claim 1, wherein the flow is turbulent in all reactors.

9. The process as claimed in claim 2, wherein the flow is turbulent in all reactors.

10. The process as claimed in claim 3, wherein the flow is turbulent in all reactors.

11. The process as claimed in claim 1, wherein the hydrogenation is carried out at temperatures of 40° to 150° C.

12. The process as claimed in claim 2, wherein the hydrogenation is carried out at temperatures of 40° to 150° C.

13. The process as claimed in claim 11, wherein the hydrogenation is carried out at temperatures of 80° to 130° C.

14. The process as claimed in claim 12, wherein the hydrogenation is carried out at temperatures of 80° to 130° C.

15. The process as claimed in claim 1, wherein the hydrogenation is carried out in the individual reactors at different temperature levels.

16. The process as claimed in claim 1, wherein the hydrogenation is carried out at pressures of 1 to 100 bar absolute.

17. The process as claimed in claim 16, wherein the hydrogenation is carried out at pressures of 5 to 20 bar absolute.

18. The process as claimed in claim 1, wherein the hydrogenation is carried out in the individual reactors at different pressure levels.

19. The process as claimed in claim 1, wherein the hydrogenation is carried out on a palladium catalyst.

20. The process as claimed in claim 19, wherein the hydrogenation is carried out on a palladium catalyst which is applied to a support of aluminum oxide.

* * * * *